United States Patent [19]

Volz

[11] 4,257,129

[45] Mar. 24, 1981

[54] PROSTHETIC KNEE JOINT TIBIAL IMPLANT

[76] Inventor: Robert G. Volz, 2705 Camino LaZorrela, Tucson, Ariz. 85718

[21] Appl. No.: 41,084

[22] Filed: May 21, 1979

[51] Int. Cl.$^3$ .............................................. A61F 1/03
[52] U.S. Cl. .................................. 3/1.911; 128/92 C
[58] Field of Search ....................... 3/1.9, 1.91, 1.911, 3/1.912, 1.913; 128/92 C

[56] References Cited

U.S. PATENT DOCUMENTS

| 2,679,245 | 5/1954 | Timmermans | 3/1.913 X |
| 4,016,606 | 4/1977 | Murray et al. | 3/1.911 |
| 4,081,866 | 4/1978 | Upshaw et al. | 3/1.911 |

FOREIGN PATENT DOCUMENTS

| 2378505 | 9/1978 | France | 3/1.911 |
| 1507309 | 4/1978 | United Kingdom | 3/1.911 |

OTHER PUBLICATIONS

Zimmer Advertisement–"Here's a Good Skate", *Journal of Bone and Joint Surgery*, vol. 53-A, No. 5, Jul. 1971.

*Primary Examiner*—Clifford D. Crowder
*Attorney, Agent, or Firm*—Woodard, Weikart, Emhardt & Naughton

[57] ABSTRACT

A prosthetic implant for replacement of the proximal end of the tibia includes a metal anchor member which is cemented into the intramedullary canal of the tibia and a replaceable high density polyethylene articulation member which is pinned to the anchoring member. The anchoring member and the replaceable articulation member slidably fit together by movement in a lateral direction by means of a dovetail fitting and a raised tab portion is provided as a stop means in order to assure proper positioning of one member with respect to the other. Once the two members are properly aligned, a vertical pin is inserted therethrough and is secured in position by a two prong horizontal clip arrangement which inserts through the articulation member and clips about a reduced diameter portion of the vertical pin member. Notches are provided in both the anchoring member as well as the replaceable articulation member for clearance of ligaments and the outer peripheral edge of the anchoring member includes a depending sharp lip and a depending groove therebehind which facilitate cementing of the anchoring member in place by compacting acrylic bone cement into the prepared surface of the tibia.

16 Claims, 12 Drawing Figures

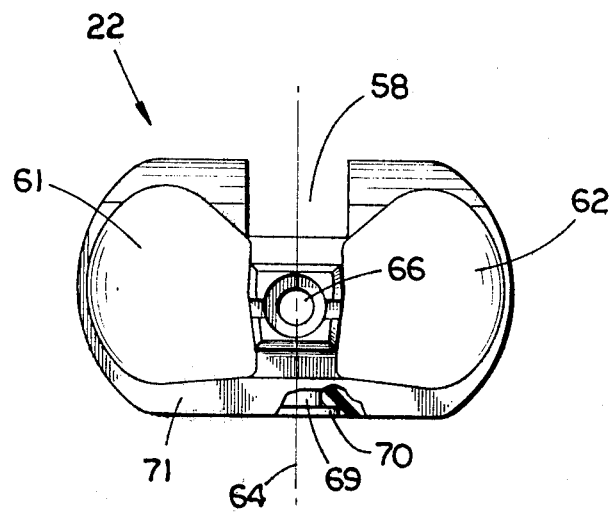
FIG. 3b
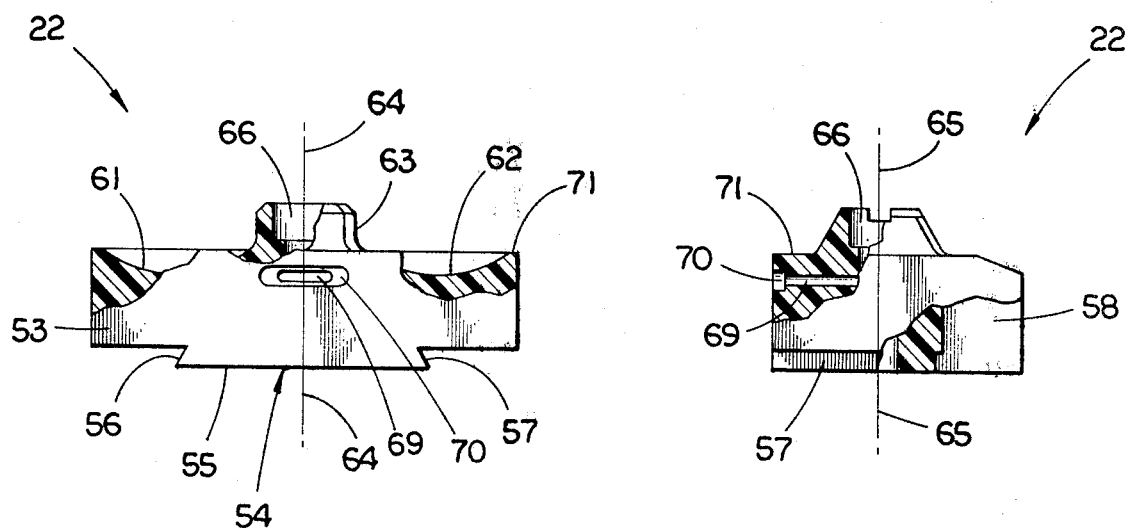
FIG. 3
FIG. 3a

PROSTHETIC KNEE JOINT TIBIAL IMPLANT

BACKGROUND OF THE INVENTION

This invention relates in general to prosthetic devices such as implants and artificial joints and more particularly to such devices which are associated with replacement of the knee joint.

The knee joint basically consists of the bone interface of the distal end of the femur and the proximal end of the tibia. Appearing to cover or at least partially protect this interface is the patella which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and articulate with the medial condyle and the lateral condyle of the tibia, respectively. The condyles of the tibia are substantially smooth and slightly cupped thereby providing a slight receptacle for receipt of the femur condyles.

When the knee joint is injured whether as a result of an accident or illness, the natural bones may become damaged to the extent that they are unable to function (articulate) properly. If the bones are affected beyond the level or degree where natural healing and new growth will remedy the damage, then a prosthetic replacement of the damaged portion is called for in order to restore normal use to the joint. Typically the entire joint is replaced by means of a surgical procedure which involves removal of the ends of the corresponding damaged bones and replacement of these ends with prosthetic implants. A typical such implant would be for the hip joint wherein a metal implant could be anchored in the intramedullary canal of the femur and would provide a generally spherical protuberance extending outwardly therefrom. The mating prosthetic portion would be a polyethylene socket member suitably anchored into the acetabulum. While prosthetic devices of this type, normally including a physiologically inert metal member and an engaging high density polyethylene member, are well known in the art, these types of devices are of a fixed and unchanging nature once they are inserted (implanted) into the patient and anchored there, whether by pinning or by acrylic bone cement or both.

Due in part to the fact that the size, shape and anatomy of virtually every patient is different, great care must be taken by the orthopedic surgeon in order to select properly sized and shaped prosthetic members for implanting. In order to achieve a suitable fit and size compatability an extensive number of variety of each type of prosthetic implant must be available to the orthopedic surgeon from which he may choose. As a result the cost of inventory as well as the logistics of ordering and storing a wide variety of prosthetic implants is cumbersome. Therefore, it would be an improvement to this present situation if prosthetic devices could be structured with removable portions such that there would be a reduction in inventory without a corresponding compromise as to the number and variety of different prosthetic combination which can be created. In order to provide such an improvement it is necessary that the prosthetic portions which are to be mixed and matched into a variety of combinations be suitably secured together so that the prosthetic member, which they in combination create, is not weaker nor more likely to fail than would be a similar prosthetic member constructed as a single integral piece.

A further concern involves the procedure when a prosthetic device becomes worn or damaged and a replacement must be made. While this is possible, it oftentimes involves elaborate surgery depending upon the particular portion of anatomy involved and the extent or nature of the damage to the prosthetic device. Furthermore, certain portions of the anatomy such as knee joints may be more susceptible to wear due to the surface area of articulation, the nature of the anatomy and the typical loads and forces which are encountered by this particular joint. Repair and/or replacement may also be desired when interfacing portions of the anatomy change and the contacting portion of the prosthesis needs to be revised as to its shape or size.

By structuring a prosthetic implant such that the portion most likely to wear or desired to be changed is quickly and easily replaceable from the remaining portion of the prosthetic implant, significant amounts of surgical time can be saved and the prosthesis can be more closely tailored to the patient's needs. Equally important is the fact that the portion of the prosthesis which is anchored into the patient, such as a tapered shaft inserted into the intramedullary canal of the tibia, does not have to be surgically removed in order to make a replacement of a worn or damaged tibia articulation portion. Such a replaceable concept, in order to be effective, must securely hold the anchored portion and the replaceable portion together so as to act as an integral member regardless of the nature or complexity of the forces and loads acting thereon. With a design which achieves the requisite strength and durability, it is then possible to mix and match the replaceable portion with various anchored portions and vice versa such that, for example, an inventory of three replaceable portions and three anchored portions for a tibia implant would be able to provide nine different combinations to the orthopedic surgeon rather than having to inventory and stock nine separate complete tibia implant members.

The prosthetic device disclosed herein provides means and apparatus for such a replaceable prosthetic concept and achieves the various objects discussed as well as others as will be apparent from the disclosure which follows.

SUMMARY OF THE INVENTION

A prosthetic implant for partial replacement of natural bone at a point of articulation according to one embodiment of the present invention comprises an anchoring insert member including an upper surface contoured to provide a laterally extending groove, a replaceable articulation member slidably received in the laterally extending groove of the anchoring insert member, a removable vertical pin member extending through the articulation member and into the anchoring insert member, and a horizontal clip member extending into the articulation member and being disposed about the vertical pin member.

A prosthetic implant for partial replacement of natural bone at a point of articulation according to another embodiment of the present invention comprises a permanent member arranged for anchoring to a natural bone portion and including a substantially flat support surface bounded to two opposite sides with raised dovetail edges and a removable articulation member having a depending dovetail boss wherein the dovetail boss is suitably sized and configured for a snug sliding fit with the raised dovetail edges of the support surface of the permanent member.

One object of the present invention is to provide an improved prosthetic device and concept.

Related objects and advantages of the present invention will be apparent from the following description.

BRIEF DESCRIPTION OF THE DRAWINGS

FIGS. 3, 3a and 3b are a fragmentary front elevation view, side elevation view and plan view respectively of a replaceable articulation member comprising a portion of the FIG. 1 prosthetic implant.

DESCRIPTION OF THE PREFERRED EMBODIMENTS

Figure 5:
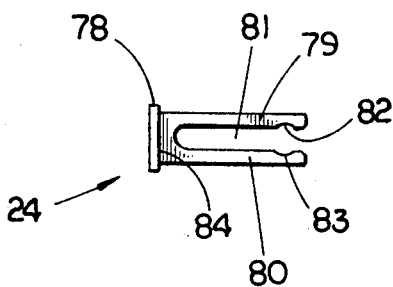
FIGS. 5 and 5a are a plan view and side elevation view respectively, of a horizontal clip member comprising a portion of the FIG. 1 prosthetic implant.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would nromally occur to one skilled in the art to which the invention relates.

Figure 1:
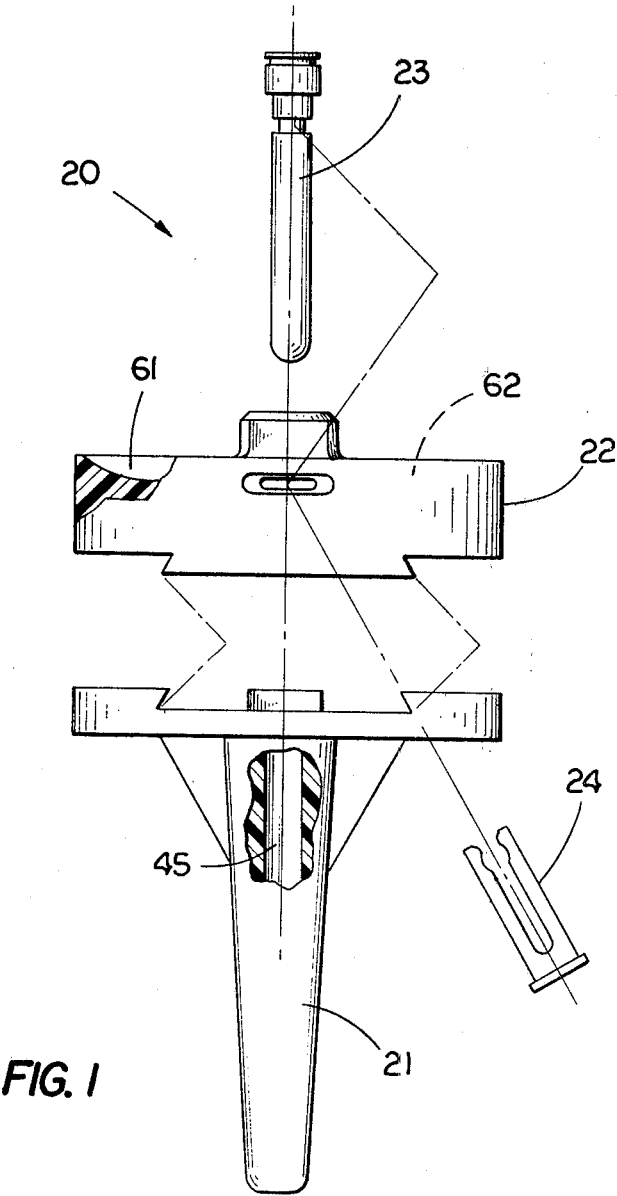
FIG. 1 is a front elevation exploded view of a replaceable tibia prosthetic implant according to a typical embodiment of the present invention.
Figure 6:
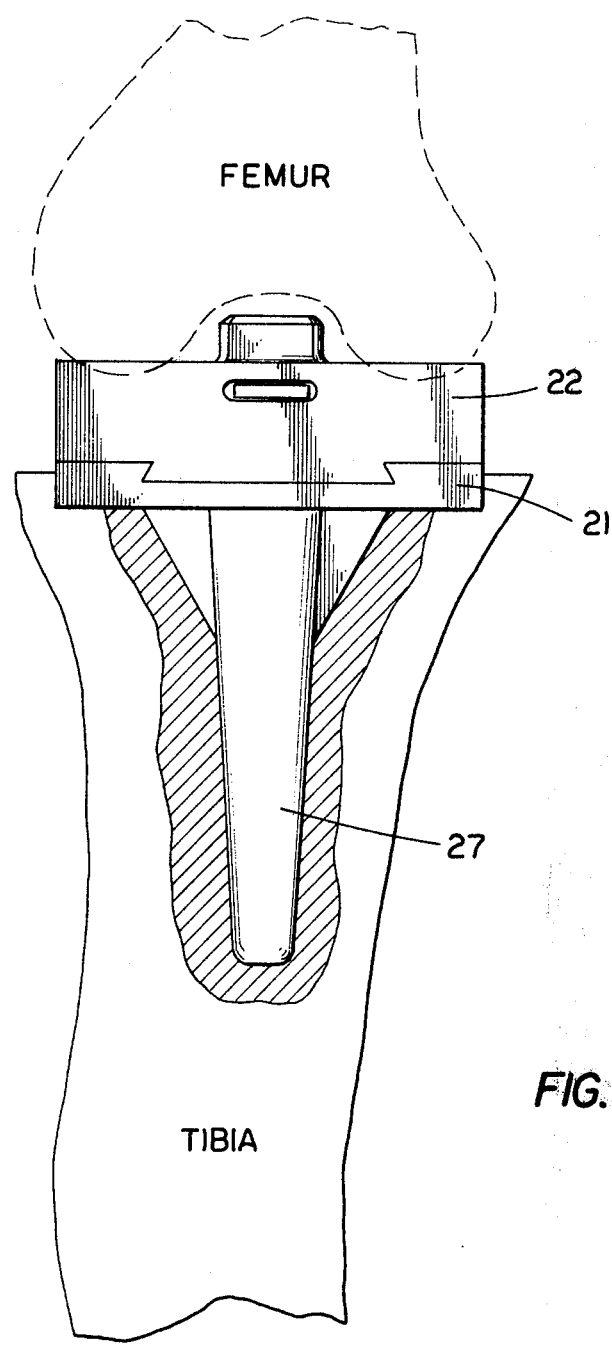
FIG. 6 is a partial, fragmentary front elevation view of the FIG. 1 prosthetic implant disposed in place in the proximal end of the table.

Referring to FIG. 1 there is illustrated a prosthetic implant 20 for the proximal end of the tibia (see FIG. 6). Implant 20 includes a permanent anchoring member 21, a replaceable articulation member 22, a vertical pin member 23 and a horizontal clip member 24. References to the terms "vertical" and "horizontal" are used in the normal context of such words wherein the tibia of an individual standing upright extends in a vertical direction. While each of these four component parts of implant 20 will be described in greater detail hereinafter, it is important to realize that FIG. 1 is an exploded view and that the assembly of these four component parts into a single prosthetic implant involves laterally sliding replaceable articulation member 22 into permanent anchoring member 21 whereby their corresponding dovetail surfaces engage one another. Once this engagement is achieved vertical pin member 23 is inserted downwardly in a vertical direction through replaceable articulation member 22 and into permanent anchoring member 21. The final assembly step is to insert horizontal clip member 24 into replaceable articulation member 22 whereby the prongs of clip member 24 will engage the reduced diameter groove of pin member 23.

Figure 2B:
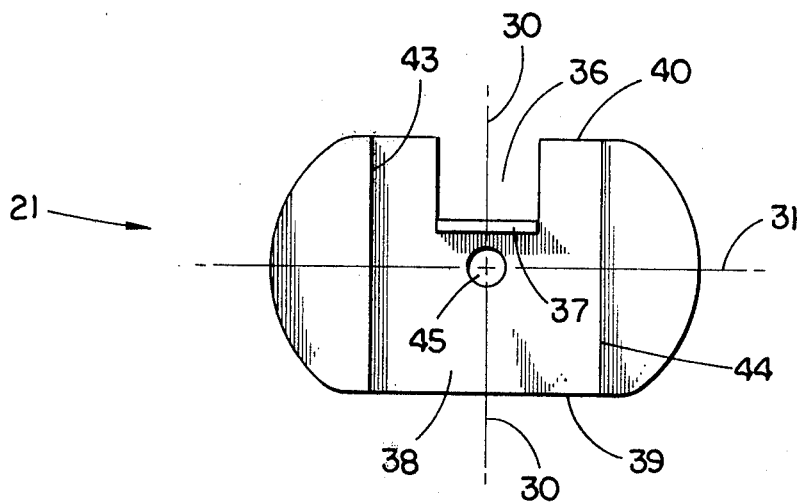
FIGS. 2, 2a and 2b are a fragmentary front elevation view, side elevation view and plan view respectively, of an anchoring insert member comprising a portion of the FIG. 1 prosthetic implant.
Figure 2:
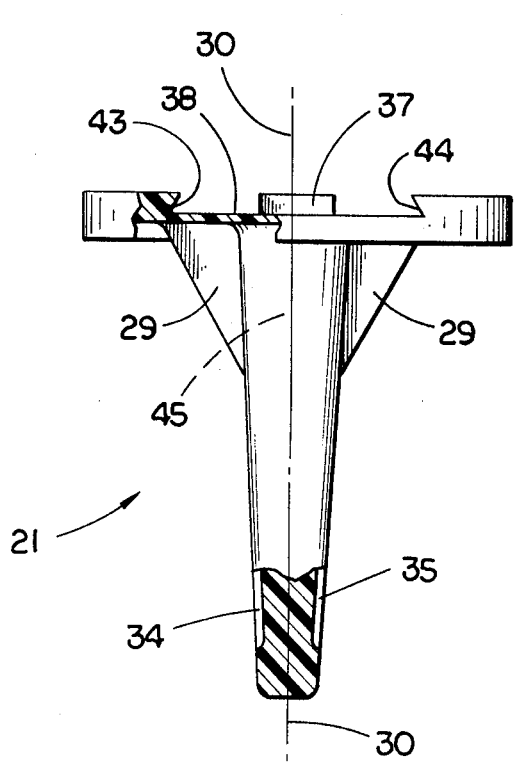
Figure 2A:
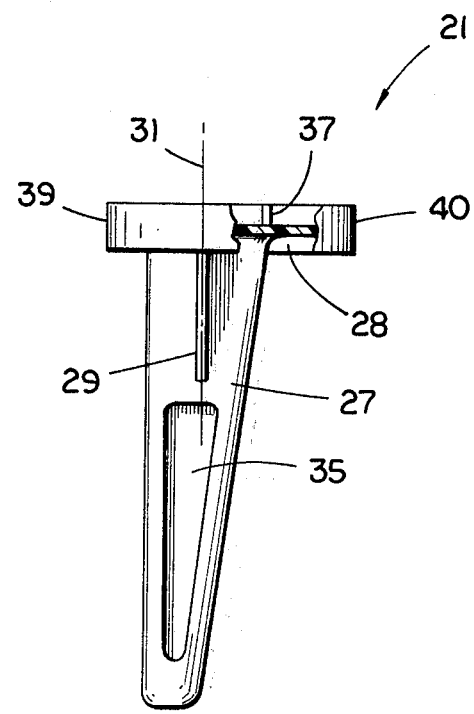

Referring to FIGS. 2, 2a and 2b permanent anchoring member 21 is illustrated in greater detail. Anchoring member 21 includes a tapered stem 27, support shelf 28 which is integrally joined to the tapered stem and two oppositely disposed webs 29 which extend laterally of the tapered stem 27 upwardly and outwardly to their point of connection to the underside of support shelf 28. While tapered stem 27 and support shelf 28 are substantially symmetrical with respect to centerline 30 there is a non-symmetrical appearance with respect to centerline 31 (see FIG. 2a). Tapered stem 27 has a substantially rectangular lateral cross-section throughout its entire length with the minor exception of depressions 34 and 35 which are provided in order to facilitate the cementing and anchoring of tapered stem 27 into the tibia, such as into the intramedullary canal of the tibia.

Support shelf 28 has a generally oblong peripheral configuration (see FIG. 2b) with the exception of a substantially square notch 36. Notch 36 is symmetrically disposed about the vertical plane which is coincident with centerline 30. The interior longitudinal edge of notch 36 includes a raised tab 37 which is also symmetrically disposed about the vertical plane of centerline 30. The center portion of support shelf 28 includes a support surface 38 which extends completely across support shelf 28 from edge 39 to edge 40. Support surface 38 has raised side edges 43 and 44 which are inclined upwardly and inwardly in order to create a dovetail-like groove configuration associated with support surface 38. The presence of notch 36 creates a U-shaped periphery configuration for support surface 38 and notch 36 provides a very significant benefit to implant 20 in that this void region provides clearance for ligaments to pass therethrough without interference.

Centrally disposed with respect to anchoring member 21 (coincident with the intersection of centerlines 30 and 31) is blind hole 45 which extends from support surface 38 into tapered stem 27 and extends to a depth in stem 27 which is slightly less than half the overall length of stem 27. Blind hole 45 is that portion of implant 20 which receives vertical pin member 23 as has been previously described. While the material choice for anchoring member 21 may vary, it is important that a relatively durable and strong material be used, such as one of the various steel alloys. It is also important that the material selected be biologically and physiologically inert and that it be properly sterilized and prepared prior to implant. Inasmuch as one aspect of the subject invention is the interchangeability of the prosthetic components, it is to be understood that the shape and size characteristics of tapered stem 27 may vary as well as the peripheral shape of support shelf 28. It is important, however, that the size and shape of support surface 38 in combination with raised side edges 43 and 44 be standardized so that proper fit and engagement with a selected articulation member can be preserved. The selection of a particular stem length and a particular support shelf configuration are to be governed by the size, shape and anatomy of the particular patient as well as the nature and extent of the damaged bones.

Figure 7:
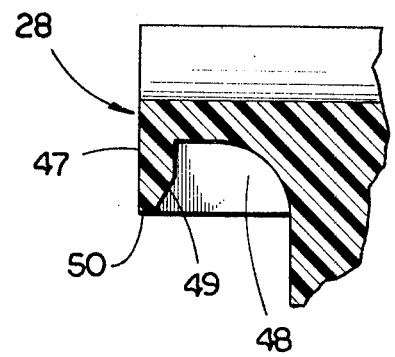
FIG. 7 is a partial, enlarged, front elevation section view of the support shelf edge of the FIG. 2 anchoring insert member.

A still further aspect of anchoring member 21 is the shape and configuration of the underside of support shelf 28. Referring to FIG. 7 an enlarged section view is provided of the edge configuration of support shelf 28. This particular edge configuration extends throughout a majority of the periphery of support shelf 28 and provides a very unique as well as desirable implant concept. Edge 46 includes a depending lip portion 47 and a depending groove 48 therebehind. Depending lip proportion 47 includes a downwardly and outwardly inclined surface 49 terminating at sharp edge 50. While edge 50, in the enlarged view of FIG. 7, appears as a narrow flat surface rather than a sharp edge, it is to be understood that the width of edge 50 is less than 0.02 inches and thus with respect to the bone surface into which this edge is inserted it assumes the appearance of a sharp or knife edge.

The advantages of lip portion 47 in combination with groove 48 are primarily realized at the time of implant. Once the tibia is properly cut and prepared for insertion of anchoring member 21, acrylic bone cement is applied over a majority of the interfacing surfaces such as the interface between the underside of support shelf 28 and the proximal end of the prepared tibia. As anchoring member 21 is forced into the tibia the acrylic bone cement trapped within groove 48 will be compacted more and more with the advancement of anchoring member 21 into the tibia. This compacting of the acrylic bone cement forces this cement into the actual bone structure of the tibia thereby enhancing the holding properties and strength and providing an extremely secure and rigid cement connection between the anchoring member and the tibia.

Referring to FIGS. 3, 3a and 3b the replaceable articulation member is illustrated in greater detail. Articulation member 22 is a single integral component piece fabricated from high density polyethylene or a similar synthetic material which has self lubricating properties with respect to the surface against which it articulates. Articulation member 22 includes a main body portion 53 and a laterally extending dovetail boss depending therefrom. Bottom surface 55 and inwardly and upwardly inclined edges 56 and 57 are all compatably sized and shaped so as to slidably fit within the dovetail groove of anchoring member 21 as defined by support surface 38 and raised side edges 43 and 44. Edges 56 and 57 are substantially parallel to each other, as were side edges 43 and 44, and edges 56 and 57 extend the full width of main body portion 53. Although this particular configuration of dovetail boss 54 would appear to create a substantially rectangular shape for this boss, boss 54 as well as main body portion 53 are relieved with a clearance notch 58 similar in size and shape as well as location to notch 36.

Disposed within the upper surface of main body portion 53 are two concave depressions 61 and 62 which are intended to generally correspond in size, shape and location to the medial condyle and the the lateral condyle of the tibia. It is these two concave depressions which constitute the articulating surface of implant 20 and which make contact with the corresponding prosthetic member which is implanted into the femur. Although not specifically illustrated as part of this invention, it is to be understood that the device and concept disclosed herein would typically be used as part of a total knee joint replacement and thus there would be a suitably sized and configured prosthetic implant associated with the femur. Such a femoral implant would provide a matching lateral condyle and medial condyle for articulation with concave depressions 61 and 62. Extending upwardly from the top surface of main body portion 53 is a raised boss portion 63 which is centrally disposed at the intersection of centerlines 64 and 65. In a manner similar to anchoring member 21, articulation member 22 is symmetrically arranged with respect to the vertical plane which is coincident with centerline 64, but such a symmetrical relationship does not exist with respect to centerline 65. Raised boss portion 63 is of a size and shape such that it is disposed within the intercondylar notch portion of the femoral implant and maintains clearance therewith such that there is not interference by this boss portion.

Extending downwardly completely through articulation member 22 and centrally disposed at the intersection of centerlines 64 and 65 is counterbored hole 66. Hole 66 vertically extends through articulation member 22 and the longitudinal axis of hole 66 is substantially perpendicular to bottom surface 55. The counterbored head portion of hole 66 receives the enlarged head portion of vertical pin member 23 in order to control the depth to which pin member 23 extends when inserted through articulation member 22 into anchoring member 21. Extending substantially perpendicular to the longitudinal axis of hole 66 is an oblong slot-like aperture 69 which extends sufficiently deep into main body portion 53 so as to extend beyond the back edge of hole 66. Also included is an oblong slot-like counterbore 70 which provides a stop surface for the advancement of horizontal clip member 24 such that clip member 24 may be properly positioned with respect to the reduced diameter of pin member 23 in order to lockingly clip around member 23 when implant 20 is in its final assembled condition. In addition to providing a stopping or abutting surface for the enlarged head portion of horizontal clip member 24, oblong slot-like counterbore 70 also provides a recessed surface into which the enlarged head of horizontal clip member 24 may be retained thereby presenting a flush exterior surface appearance.

So long as dovetail boss 54 remains properly sized and configured for sliding engagement with the dovetail groove of anchoring member 21, the remaining aspects of articulation member 22 may be varied in order to tailor the implant to the particular patient. In this regard it is envisioned that the overall depth from bottom surface 55 to top surface 71 may be varied as well as the radius of concave depressions 61 and 62. There may be yet further structural changes and variations desired depending upon the nature of the patient and the particular damage. However, it should be apparent that the anchoring member 21 can be selected based upon such factors as tibia diameter independently of tibia length or the amount of bone which has to be removed prior to prosthetic implant. Therefore if additional distance or length is required by build up in order to place concave depressions 61 and 62 at their proper location for articulation with the prosthetic member inserted into the femur then all that need be done is to select an articulation member which has a suitable thickness dimension from bottom surface 55 to top surface 71 in order to provide this desired or necessary height dimension.

Figure 4:
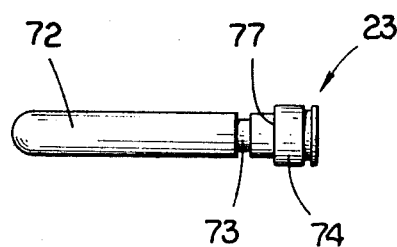
FIG. 4 is a side elevation view of a vertical pin member comprising a portion of the FIG. 1 prosthetic implant.

Referring to FIG. 4 vertical pin member 23 is illustrated in greater detail. Vertical pin member 23 includes a main body portion 72, a reduced diameter portion 73 and an enlarged head portion 74. All portions of vertical pin member 23 are substantially cylindrical and it is surface 77 which abuts against the base of the counterbore of hole 66. With vertical pin member 23 fully inserted into anchoring member 21 and articulation member 22 (surface 77 abuts against the counterbore base)

there is clearance left between the bottom of blind hole 45 and the end of pin member 23. Also, in this same "fully inserted" configuration the center of reduced diameter portion 73 is disposed coincident with the horizontal centerline of oblong slot-like aperture 69.

Figure 5A:
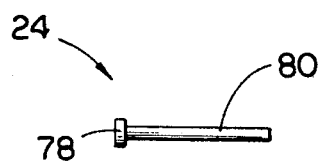

Referring to FIGS. 5 and 5a horizontal clip member 24 is illustrated in greated detail. Horizontal clip member 24 includes an enlarged head portion 78 and two outwardly enxtending prongs 79 and 80 which are substantially parallel to each other and perpendicular to the surface of enlarged head portion 78 and which define a clearance slot 81 therebetween. Enlarged head portion 78 is substantially rectangular as are prongs 79 and 80 and near the far end of each prong are complimentary part circular recesses 82 and 83 respectively. The dimension from surface 84 to the approximate center of part circular recesses 82 and 83 is substantially the same as the dimension from the base of oblong slot-like counterbore 70 to centerline 65. In this manner part circular recesses 82 and 83 are positioned with respect to vertical pin member 23 such that prongs 79 and 80 clip around reduced diameter portion 73 and in fact part circular recesses 82 and 83 actually contact, with a type of spring clip action, the surface of reduced diameter portion 73. In this manner the entire prosthetic implant assembly including anchoring member 21, articulation member 22, pin member 23 and clip member 24 are all held securely together as if constructed as a single integral member.

One aspect which is important in order to create the appearance of a very solid and rigid single member is the relationship of the clearance and interference fits between the various component parts. In this regard it is to be understood that the dimensions and permissible tolerances on dovetail boss 54 and the dovetail groove of anchoring member 21 are such so as to create a fit range of between 0.001 inches of clearance to 0.004 inches of interference. Similarly vertical pin member 23 fits within blind hole 45 such that there is between 0.001 inches of clearance and 0.005 inches of clearance. Similar close fitting tolerances are in existence at most critical interface points so that there is virtually no looseness or excessive play at any location in the entire assembly.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A prosthetic implant for partial placement of natural bone at a point of articulation, said prosthetic implant comprising:
   an anchoring insert member including an upper surface contoured to provide a laterally extending groove;
   a replaceable articulation member slidably received in said laterally extending groove of said anchoring insert member;
   a removable vertical pin member extending through said articulation member and into said anchoring insert member; and
   a removable horizontal clip member extending into said articulation member and disposed about said vertical pin member.

2. The prosthetic implant of claim 1 wherein said horizontal clip member includes two substantially parallel prongs and said vertical pin member includes a reduced diameter annular groove disposed between said two prongs, said two prongs being designed to clip around said annular groove.

3. The prosthetic implant of claim 1 wherein said replaceable articulation member includes two concave depressions disposed in the upper surface of said replaceable articulation member, a generally cylindrical aperture passing between said two concave depressions and an oblong slot-like aperture passing between said two concave depressions and substantially perpendicular to the longitudinal axis of said cylindrical aperture.

4. The prosthetic implant of claim 1 wherein said replaceable articulation member includes a depending dovetail-like boss portion and said laterally extending groove includes inclined side edges, said dovetail-like boss portion and said laterally extending groove being suitably sized and arranged relative to each other to engage each other by a dovetail fitting arrangement.

5. The prosthetic implant of claim 4 wherein the fit between said laterally extending groove and said dovetail-like boss portion is between 0.005 inches interference fit and 0.002 inches clearance fit.

6. The prosthetic implant of claim 5 wherein said anchoring insert member further includes a depending stem portion having a generally rectangular lateral cross-section throughout and a substantially flat support shelf joined thereto.

7. The prosthetic implant of claim 1 wherein said upper surface of said anchoring insert member includes a centrally disposed edge notch for providing clearance of ligaments.

8. The prosthetic implant of claim 7 which further includes a tab portion coincident with one edge of said notch and extending upwardly from said upper surface, said tab portion providing stop means to continued sliding advancement of said replaceable articulation member relative to said anchoring insert member.

9. A prosthetic implant for partial replacement of natural bone at a point of articulation, said prosthetic implant comprising:
   a permanent member arranged for anchoring to a natural bone portion;
   a removable articulation member slidably received by said permanent member;
   removable pinning means extending through said removable articulation member and into said permanent member for preventing lateral movement of said removable articulation member relative to said permanent member; and
   removable clip means extending into said removable articulation member and engaging said removable pinning means for preventing longitudinal movement of said removable pinning means relative to said removable articulation member.

10. The prosthetic implant of claim 9 wherein said removable pinning means includes a generally cylindrical pin having a main body portion, an enlarged head portion and a reduced diameter portion therebetween.

11. The prosthetic implant of claim 9 wherein said permanent member includes a dovetail-like groove and said removable articulation member includes a dovetail-like boss, said groove and said boss being suitably arranged and sized with respect to each other for a snug dovetail fit arrangement.

12. The prosthetic implant of claim 9 wherein said permanent member includes a stem portion and a support shelf joined thereto, said support shelf including a depending sharp lip portion and a depending groove therebehind both extending throughout a majority of the periphery of said support shelf.

13. A prosthetic implant for partial replacement of a natural bone on one side of a point of articulation, said prosthetic implant comprising:

a permanent member arranged for anchoring to said natural bone and including a substantially flat support surface bounded on two opposite sides with raised dovetail edges, said support surface having a U-shaped periphery and the recessed void of said U-shaped periphery including a raised tab portion; and a removable articulation member having a depending dovetail boss, said dovetail boss being suitably sized and configured for a snug sliding fit with said raised dovetail edges and said support surface of said permanent member.

14. The prosthetic implant of claim 13 wherein said raised dovetail edges are substantially parallel to each other and extend the full width of said support surface.

15. The prosthetic implant of claim 13 wherein said raised dovetail edges are substantially parallel to each other and extend the full width of said support surface, said raised dovetail edges and said dovetail boss engaging each other by lateral sliding movement of said boss onto said support surface, said raised tab portion contacting said dovetail boss at a predetermined position preventing continued lateral advancement of said removable articulation member.

16. The prosthetic implant of claim 15 which further includes a vertical pin member extending through said removable articulation member and into said permanent member and a horizontal clip member extending through said removable articulation member and arranged to clip around said vertical pin member.

* * * * *